United States Patent
Zupancic

(10) Patent No.: US 9,493,409 B2
(45) Date of Patent: Nov. 15, 2016

(54) PROCESS FOR THE SYNTHESIS OF 1-(2-((2,4-DIMETHYLPHENYL)THIO) PHENYL)PIPERAZINE

(71) Applicant: Lek Pharmaceuticals d.d., Ljubljana (SI)

(72) Inventor: Borut Zupancic, Ljubljana (SI)

(73) Assignee: Lek Pharmaceuticals d.d. (SI)

( * ) Notice: Subject to any disclaimer, the term of this patent is extended or adjusted under 35 U.S.C. 154(b) by 0 days.

(21) Appl. No.: 14/781,716

(22) PCT Filed: Apr. 4, 2014

(86) PCT No.: PCT/EP2014/056769
§ 371 (c)(1),
(2) Date: Oct. 1, 2015

(87) PCT Pub. No.: WO2014/161976
PCT Pub. Date: Oct. 9, 2014

(65) Prior Publication Data
US 2016/0060215 A1    Mar. 3, 2016

(30) Foreign Application Priority Data
Apr. 4, 2013 (EP) .................................... 13162296

(51) Int. Cl.
C07C 319/20 (2006.01)
C07C 323/37 (2006.01)
C07D 295/096 (2006.01)
C07C 323/09 (2006.01)

(52) U.S. Cl.
CPC ........... C07C 319/20 (2013.01); C07C 323/09 (2013.01); C07C 323/37 (2013.01); C07D 295/096 (2013.01)

(58) Field of Classification Search
CPC .................................................. C07C 319/20
See application file for complete search history.

(56) References Cited

FOREIGN PATENT DOCUMENTS

WO    03029232 A1    4/2003
WO    2007144005 A1    12/2007

OTHER PUBLICATIONS

Novi et al (1987): STN International HCAPLUS database, Columbus (OH), Accession No. 1987:543588.*

International Search Report and Written Opinion, PCT/EP2014/056769, date of mailing Apr. 29, 2014, 11 pages.
Novi, Marino et al., Electrochemical Reduction of Some o-Bis(phenylsulphonyl)benzene Derivatives, Journal of Chemical Society, Jan. 1987, pp. 623-631.
Kold Udam, Henriette et al., Biosynthesis and Identification of an N-Oxide/N-Glucuronide Metabolite and First Synthesis of an N—O-Glucuronide Metabolite of Lu AA21004, Drug Metabolism and Disposition, The American Society for Pharmacology and Experimental Therapeutics, 2011, pp. 2264-2274, vol. 39, No. 12, USA.

* cited by examiner

*Primary Examiner* — Golam M M Shameem
(74) *Attorney, Agent, or Firm* — Luedeka Neely Group, P.C.

(57) ABSTRACT

The present invention provides new intermediate compounds or formulae (III) and (IVa), and salts thereof, and their use in a new synthetic process for the production of 1-(2-((2,4-dimethylphenyl)thio)phenyl)piperazine (vortioxetine) an experimental drug under development for the treatment of depression and anxiety.

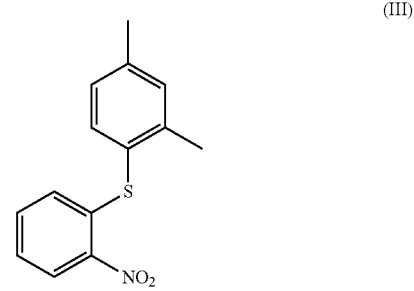

(III)

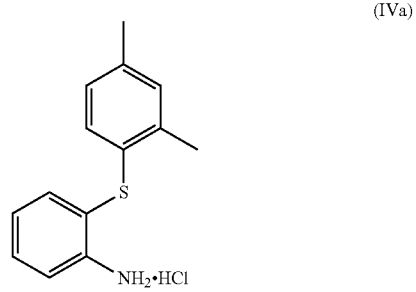

(IVa)

4 Claims, No Drawings

PROCESS FOR THE SYNTHESIS OF 1-(2-((2,4-DIMETHYLPHENYL)THIO)PHENYL)PIPERAZINE

This application is a national phase entry of PCT International application number PCT/EP2014/056769, filed Apr. 4, 2014. This application also claims the benefit of the earlier filing date of EP13162296.1, filed Apr. 4, 2013.

FIELD OF THE INVENTION

This invention relates to a new and advantageous process for the synthesis of 1-(2-((2,4-dimethylphenyl)thio)phenyl)piperazine (vortioxetine) an experimental drug under development for the treatment of depression and anxiety.

BACKGROUND OF THE INVENTION

Vortioxetine is disclosed as Example 1e in WO 2003/029232 A1 and is described as being prepared analogously to Example 1. The process used to prepare Example 1 involves the preparation of 1-(2-((2-(trifluoromethyl)phenyl)thio)phenyl)piperazine on a solid polystyrene support, followed by decomplexation using visible light irradiation, and purification by preparative LC-MS and ion-exchange chromatography. The overall yield for the preparation of vortioxetine is described as 17%.

Several alternative palladium catalyzed processes for the preparation of vortioxetine are described in Examples 17 to 25 of WO 2007/144005 A1. These processes describe the preparation of vortioxetine from 2,4-dimethylthiophenol and 2-bromoiodobenzene (or 1,2-dibromobenzene) starting materials via a 1-(2-bromo-phenylsulfanyl)-2,4-dimethylbenzene intermediate. Each of these processes involves the use of a palladium catalyst and a phosphine ligand.

The preparation of vortioxetine is also described by Bang-Andersen et al. in J. Med. Chem. (2011), Vol. 54, 3206-3221. Here, in a first step, tert-butyl 4-(2-bromophenyl)piperazine-1-carboxylate intermediate is prepared from Boc-piperazine and 2-bromoiodobenzene in a palladium catalyzed coupling reaction. tert-Butyl 4-(2-bromophenyl)piperazine-1-carboxylate is then reacted with 2,4-dimethylthiophenol, again in the presence of palladium catalyst and a phosphine ligand, to provide Boc-protected vortioxetine. In the final step, vortioxetine is deprotected using hydrochloric acid to give vortioxetine hydrochloride.

Each of the above processes has disadvantages. The process described in WO 2003/029232 is low yielding and unsuitable for the large scale production of vortioxetine, whereas the processes described in WO 2007/144005 A1 and by Bang-Andersen et al. require the use of expensive starting materials, palladium catalyst and phosphine ligand. In addition, the toxicity of palladium is well known, Liu et al. Toxicity of Palladium, *Toxicology Letters*, 4 (1979) 469-473, and the European Medicines Agency's Guideline on the Specification for Residues of Metal Catalysts sets clear limits on the permitted daily exposure to palladium arising from palladium residue within drug substances, www.ema.europa.eu.

Thus it would be desirable to avoid the use of a palladium catalyst in the synthesis of vortioxetine and the subsequent purification steps required to remove palladium residue from the final pharmaceutical product.

SUMMARY OF THE INVENTION

The present invention provides new intermediate compounds, and salts thereof, and their use in a new synthetic process for the production of vortioxetine. The new process provides vortioxetine in a high yield without the use of palladium catalyst and phosphine ligand, nor expensive starting materials. Furthermore, the new intermediate compounds are provided in crystalline form allowing for improved processability, manufacture, and purity of vortioxetine end product.

DETAILED DESCRIPTION OF THE INVENTION

Embodiments and examples of the present invention are described below.

Embodiment 1

Use of a compound, or salt thereof, of formula (IV)

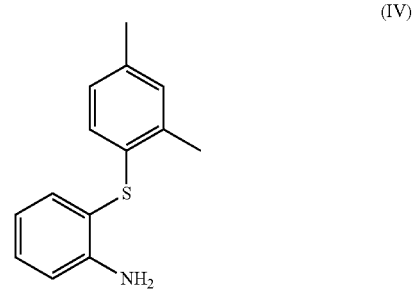

(IV)

in the manufacture of a compound, or salt thereof, of formula (V)

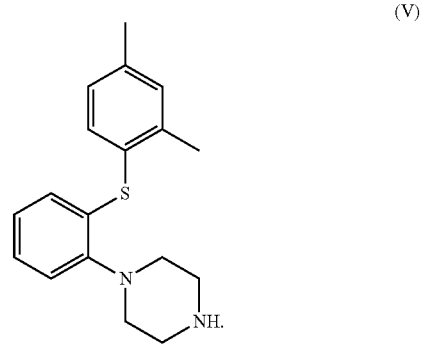 [SMILES: Cc1ccc(Sc2ccccc2N2CCNCC2)c(C)c1]

(V)

Embodiment 2

A compound, or alternative salt thereof, of formula (IVa)

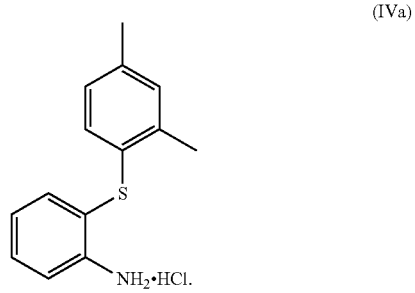

(IVa)

Embodiment 3

A process for the manufacture of a compound of formula (IV), or salt thereof,

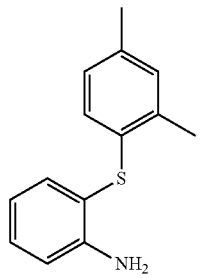

(IV)

which comprises the reduction of a compound of formula (III), or salt thereof,

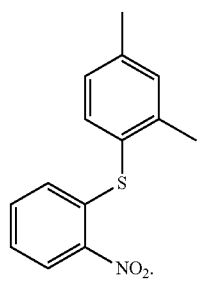

(III)

Embodiment 4

A process according to embodiment 3, wherein the reducing agent is thiourea dioxide or sodium dithionite.

Embodiment 5

A process according to Embodiment 3 or Embodiment 4 wherein the reaction is carried out in the presence of a protic or aprotic solvent.

Embodiment 6

A process according to Embodiment 5 wherein the solvent is a protic solvent selected from $C_1$-$C_6$ alcohol.

Embodiment 7

A process according to Embodiment 6 wherein the protic solvent is methanol.

Embodiment 8

A process according to Embodiment 5 wherein the solvent is an aprotic solvent selected from DMSO and DMF.

Embodiment 9

A process according to any one of Embodiments 3 to 8 wherein the reaction is carried out at a temperature of 25 to 150° C.

Embodiment 10

A process according to any one of Embodiments 3 to 8 wherein the reaction is carried out at a temperature of 55 to 65° C.

Embodiment 11

A process according to Embodiment 3 wherein the reducing agent is iron or zinc.

Embodiment 12

A process according to Embodiment 11 wherein the reduction is carried out in the presence of a suitable solvent.

Embodiment 13

A process according to Embodiment 12 wherein the solvent is $C_1$-$C_6$ alcohol.

Embodiment 14

A process according to any one of Embodiments 11 to 13 wherein the reaction is carried out in the presence of an acid.

Embodiment 15

A process according to Embodiment 14 wherein the acid is acetic, phosphoric or hydrochloric acid.

Embodiment 16

A process according to any one of Embodiments 11 to 15 wherein the reaction is carried out at a temperature of 0 to 100° C.

Embodiment 17

A process according to any one of Embodiments 11 to 15 wherein the reaction is carried out at a temperature of 20 to 30° C.

Embodiment 18

A process according to any one of Embodiments 3 to 17 which comprises the additional step of reacting the compound of formula (IV) or salt thereof, with a piperazine ring forming agent, to provide a compound of formula (V), or salt thereof,

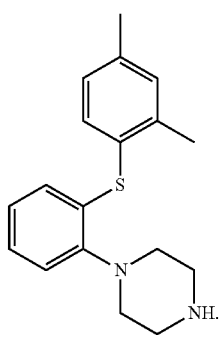

(V)

Embodiment 19

A process according to Embodiment 18 wherein the piperazine ring forming agent is selected from bis(2-chloroethyl)amine or a salt thereof, diethanolamine and morpholine.

Embodiment 20

A process according to Embodiment 19 wherein the piperazine ring forming agent is the hydrochloride salt of bis(2-chloroethyl)amine.

Embodiment 21

A process according to Embodiment 20 wherein the reaction is carried out in methyldiglycol at a temperature of 25 to 200° C.

Embodiment 22

A process according to Embodiment 20 wherein the reaction is carried out at a temperature of 120 to 140° C.

Embodiment 23

A process according to any one of Embodiments 18 to 22 which comprises the additional step of converting the compound of formula (V), or salt thereof, to its hydrobromide salt.

Embodiment 24

Use of a compound, or salt thereof, of formula (III)

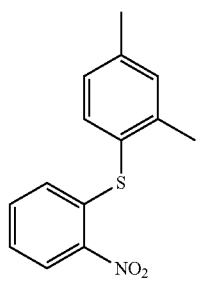
(III)

in the manufacture of a compound, or salt thereof, of formula (V)

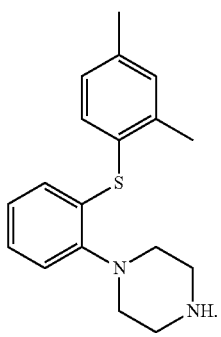
(V)

Embodiment 25

A compound of formula (III), or salt thereof,

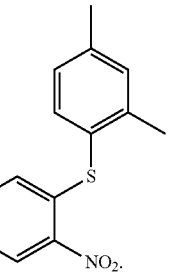
(III)

Embodiment 26

A compound according to Embodiment 25 in crystalline form.

Embodiment 27

A process for the manufacture of a compound of formula (III), or salt thereof,

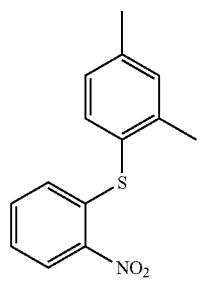
(III)

which comprises the reaction of a compound of formula (I), or salt thereof,

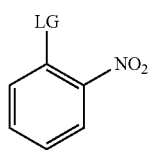
(I)

wherein LG represents a suitable leaving group, with a compound of formula (II), or salt thereof,

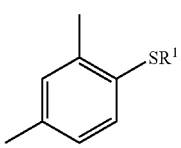
(II)

wherein $R^1$ represents hydrogen or a mono-valent metal ion, in the presence of a suitable base.

Embodiment 28

A process according to Embodiment 27, wherein LG is selected from F, Cl, Br, OTs and OTf.

Embodiment 29

A process according to Embodiment 27, wherein LG is selected from F and Cl.

Embodiment 30

A process according to any one of Embodiments 27 to 29 wherein $R^1$ represents hydrogen.

Embodiment 31

A process according to any one of Embodiments 27 to 30, wherein the base is $Na_2CO_3$ or $K_2CO_3$.

Embodiment 32

A process according to any one of Embodiments 27 to 31 wherein the reaction is carried out in the presence of a protic or aprotic solvent.

Embodiment 33

A process according to Embodiment 32 wherein the solvent is a protic solvent selected from $C_1$-$C_6$ alcohol.

Embodiment 34

A process according to Embodiment 33 wherein the protic solvent is methanol.

Embodiment 35

A process according to Embodiment 32 wherein the solvent is an aprotic solvent is DMSO or DMF.

Embodiment 36

A process according to any one of Embodiments 27 to 35 wherein the reaction is carried out at a temperature of −30 to 100° C.

Embodiment 37

A process according to any one of Embodiments 27 to 35 wherein the reaction is carried out at a temperature of 20 to 30° C.

Embodiment 38

A process for the manufacture of a compound of formula (IV), or salt thereof,

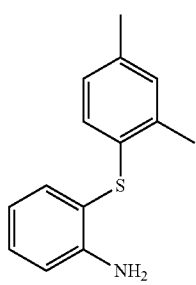
(IV)

which comprises the following steps:
(i) the reaction of a compound of formula (I), or salt thereof,

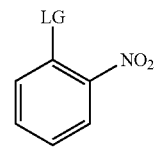
(I)

wherein LG represents a suitable leaving group, with a compound of formula (II), or salt thereof,

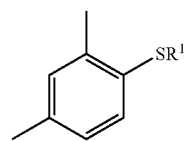
(II)

wherein $R^1$ represents hydrogen or a mono-valent metal ion, in the presence of a suitable base to provide a compound of formula (III), or a salt thereof,

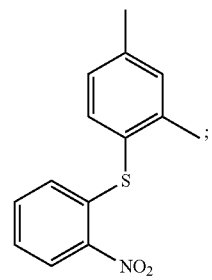
(III)

and
(ii) the reduction of the compound of formula (III), or salt thereof, to provide the compound of formula (IV), or salt thereof.

Embodiment 39

A process according to Embodiment 38, wherein LG is selected from F, Cl, Br, OTs and OTf.

Embodiment 40

A process according to Embodiment 38, wherein LG is selected from F and Cl.

Embodiment 41

A process according to any one of Embodiments 38 to 40 wherein $R^1$ represents hydrogen.

Embodiment 42

A process according to any one of Embodiments 38 to 41, wherein the base is $Na_2CO_3$ or $K_2CO_3$.

Embodiment 43

A process according to any one of Embodiments 38 to 42 wherein the reactions are carried out in the presence of a protic or aprotic solvent.

Embodiment 44

A process according to Embodiment 43 wherein the solvent is a protic solvent selected from $C_1$-$C_6$ alcohol.

Embodiment 45

A process according to Embodiment 44 wherein the protic solvent is methanol.

Embodiment 46

A process according to Embodiment 43 wherein the solvent is an aprotic solvent is DMSO or DMF.

Embodiment 47

A process according to any one of Embodiments 38 to 46 wherein the reaction of step (i) is carried out at a temperature of −30 to 100° C.

Embodiment 48

A process according to any one of Embodiments 38 to 46 wherein the reaction of step (i) is carried out at a temperature of 20 to 30° C.

Embodiment 49

A process according to any one of Embodiments 38 to 48, wherein the reducing agent used in step (ii) is thiourea dioxide or sodium dithionite.

Embodiment 50

A process according to any one of Embodiments 38 to 49 wherein the reaction of step (ii) is carried out at a temperature of 25 to 150° C.

Embodiment 51

A process according to any one of Embodiments 38 to 49 wherein the reaction of step (ii) is carried out at a temperature of 55 to 65° C.

Embodiment 52

A process according to any one of Embodiments 38 to 51 wherein the reaction steps (i) and (ii) are carried out in the same reaction vessel.

Embodiment 53

A process according to any one of Embodiments 38 to 52 which comprises the additional step of reacting the compound of formula (IV) or salt thereof, with a piperazine ring forming agent, to provide a compound of formula (V), or salt thereof,

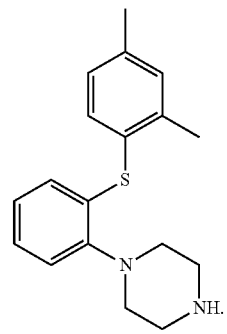

(V)

Embodiment 54

A process according to Embodiment 53 wherein the piperazine ring forming agent is selected from bis(2-chloroethyl)amine or a salt thereof, diethanolamine or morpholine.

Embodiment 55

A process according to Embodiment 54 wherein the piperazine ring forming agent is the hydrochloride salt of bis(2-chloroethyl)amine.

Embodiment 56

A process according to Embodiment 55 wherein the reaction is carried out in methyldiglycol at a temperature of 25 to 200° C.

Embodiment 57

A process according to Embodiment 56 wherein the reaction is carried out at a temperature of 120 to 140° C.

Embodiment 58

A process according to any one of Embodiments 53 to 57 which comprises the additional step of converting the compound of formula (V), or salt thereof, to its hydrobromide salt.

Embodiment 59

A process for the manufacture of a compound of formula (V), or salt thereof,

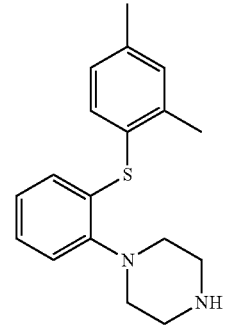

(V)

which comprises the following steps:
(i) the reaction of a compound of formula (I), or salt thereof,

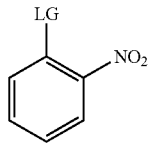
(I)

wherein LG represents a suitable leaving group,
with a compound of formula (II), or salt thereof,

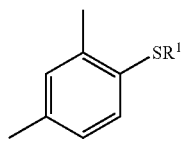
(II)

wherein $R^1$ represents hydrogen or a mono-valent metal ion, in the presence of a suitable base,
to provide a compound of formula (III), or salt thereof,

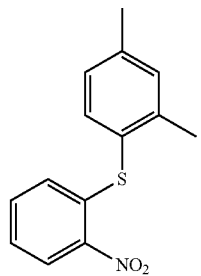
(III)

(ii) the reduction of a compound of formula (III), or salt thereof, to provide a compound of formula (IV), or salt thereof,

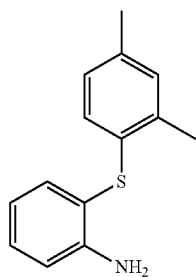
(IV)

(iii) reacting the compound of formula (IV) or salt thereof, with a piperazine ring forming agent.

Embodiment 60

A process according to Embodiment 59 wherein:
LG is selected from F, Cl, Br, OTs and OTf;
$R^1$ represents hydrogen;
the base is $Na_2CO_3$ or $K_2CO_3$;
the reducing agent used in step (ii) is thiourea dioxide or sodium dithionite;
the piperazine ring forming agent is selected from bis(2-chloroethyl)amine or a salt thereof, diethanolamine or morpholine;
step (i) is carried out at a temperature of −30 to 100° C.;
step (ii) is carried out at a temperature of 25 to 150° C.;
step (iii) is carried out at a temperature of 25 to 200° C.; and
steps (i), (ii) and (iii) are carried out in the presence of a protic or aprotic solvent.

Embodiment 61

A process according to Embodiment 59 or 60 wherein the reaction steps (i) and (ii) are carried out in the same reaction vessel.

Embodiment 62

A process according to Embodiment 59 wherein:
LG is selected from F, Cl, Br, OTs and OTf;
$R^1$ represents hydrogen;
the base is $Na_2CO_3$ or $K_2CO_3$;
the reducing agent used in step (ii) is iron or zinc; and
the piperazine ring forming agent is selected from bis(2-chloroethyl)amine or a salt thereof, diethanolamine or morpholine;
step (i) is carried out at a temperature of −30 to 100° C. in the presence of a protic or aprotic solvent;
step (ii) is carried out at a temperature of 0 to 100° C. in the presence of a protic solvent; and
step (iii) is carried out at a temperature of 25 to 200° C. in the presence of a protic or aprotic solvent.

Embodiment 63

A process according to Embodiment 62 wherein the protic solvent used in step (ii) is AcOH or a mixture of $C_1$-$C_6$ alcohol and AcOH.

For the purposes of interpreting the terms used in the description of the invention, the following definitions will apply. All other terms as used herein are to be interpreted in accordance with their everyday meaning to the person of ordinary skill in the art.

As used herein, the term "acid" represents a molecular entity or chemical species capable of donating a proton.

As used herein, the term "aprotic solvent" represents any solvent which contains no hydrogen atom that is capable of hydrogen bonding. Examples of aprotic solvents include, but are not limited to, DMSO and DMF.

As used herein, the term "base" represents a molecular entity or chemical species capable of accepting a proton.

As used herein, the term "leaving group" represents an atom or group (charged or uncharged) that becomes detached from an atom in what is considered to be the residual or main part of the substrate in a specified reaction. More particularly, as used herein the "leaving group" represents an atom or group which can be substituted in a reaction of nucleophilic aromatic substitution. Examples of leaving groups as used herein include, but are not limited to, F, Cl, Br, OTs and OTf.

As used herein, the term "reduction" represents the complete transfer of one or more electrons to a molecular entity.

As used herein, the term "reducing agent" represents the molecular entity or chemical species that donates one or more electrons to a molecular entity in a reduction reaction.

As used herein, the term "protic solvent" represents any solvent which contains one or more hydrogen atoms that are capable of hydrogen bonding. Examples of protic solvents include, but are not limited to, $C_1$-$C_6$ alcohols and AcOH.

The following abbreviations are used in the description of the invention.
AcOH=acetic acid
DMF=dimethylformamide
DMSO=dimethyl sulfoxide
EtOAc=ethyl acetate
iPrOAc=isopropyl acetate
LG=leaving group
MeOH=methanol
MeTHF=methyltetrahydrofuran
OTf=triflate
OTs=tosylate A general representation of the full length process of the invention from starting materials to final product is shown in Scheme 1 below. The first two reaction steps may be carried out in the same reaction vessel using one-pot methodologies.

The general synthetic route described in Scheme 1 starts with the S-arylation of 2,4-dimethylthiophenol (II, also named 2,4-dimethylbenzenethiol). This gives the intermediate (2,4-dimethylphenyl)(2-nitrophenyl)sulfane (III). The nitro group in III is then reduced to an amino group to give intermediate 2-((2,4-dimethylphenyl)thio)aniline (IV), which is then transformed to vortioxetine (V) by piperazine ring formation.

It is also possible to obtain 2-((2,4-dimethylphenyl)thio) aniline (IV) without isolation of III. In this one-pot process compound IV is isolated after carrying out the first two chemical reaftions steps (substitution and reduction) in the same reaction vessel. Compound IV can be isolated as a free amine or as a salt of the acid used. Preferably vortioxetine is isolated as a hydrobromide salt (VI).

The route of synthesis is described in greater detail in Scheme 1a.

Scheme 1

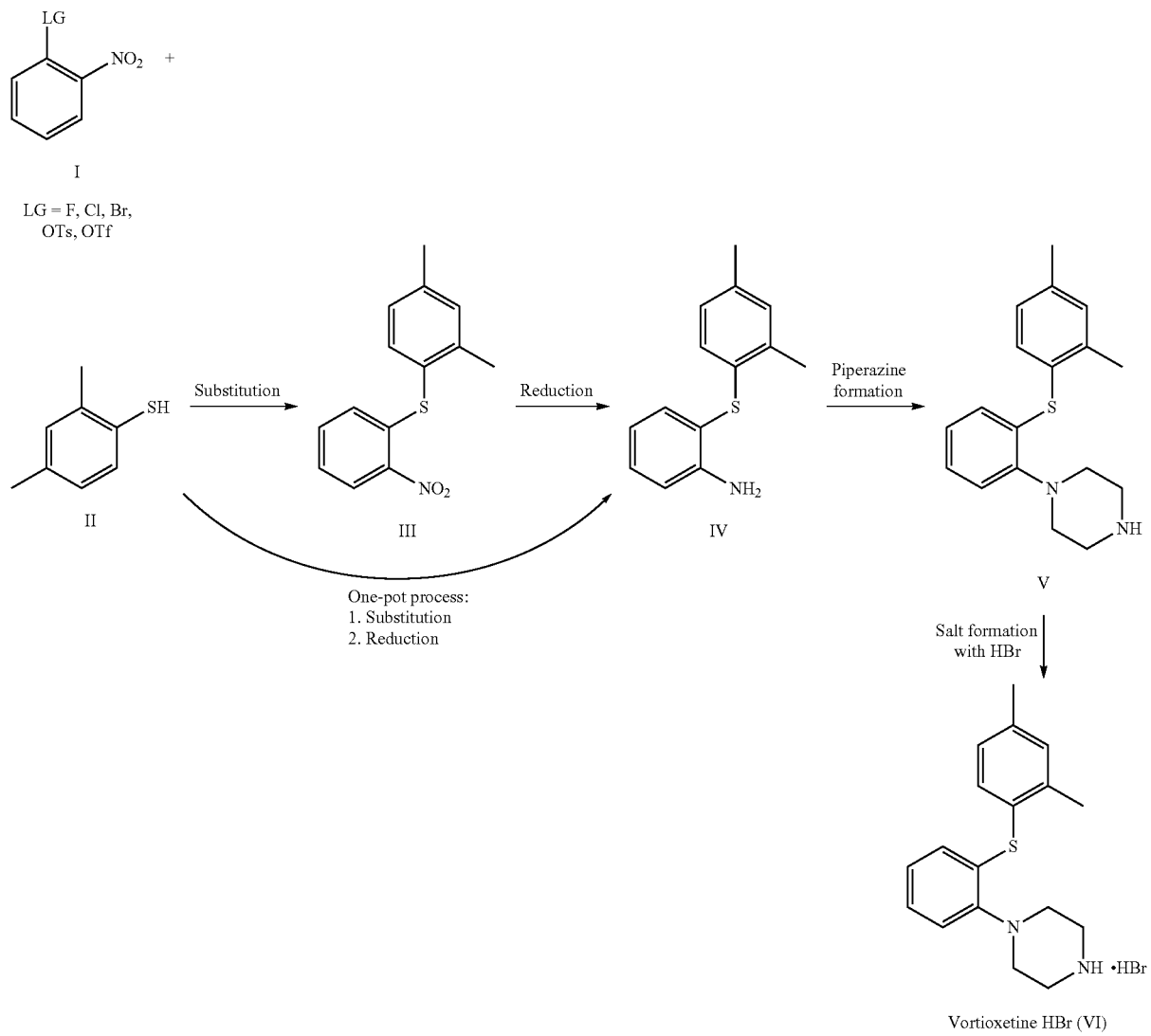

Scheme 1a

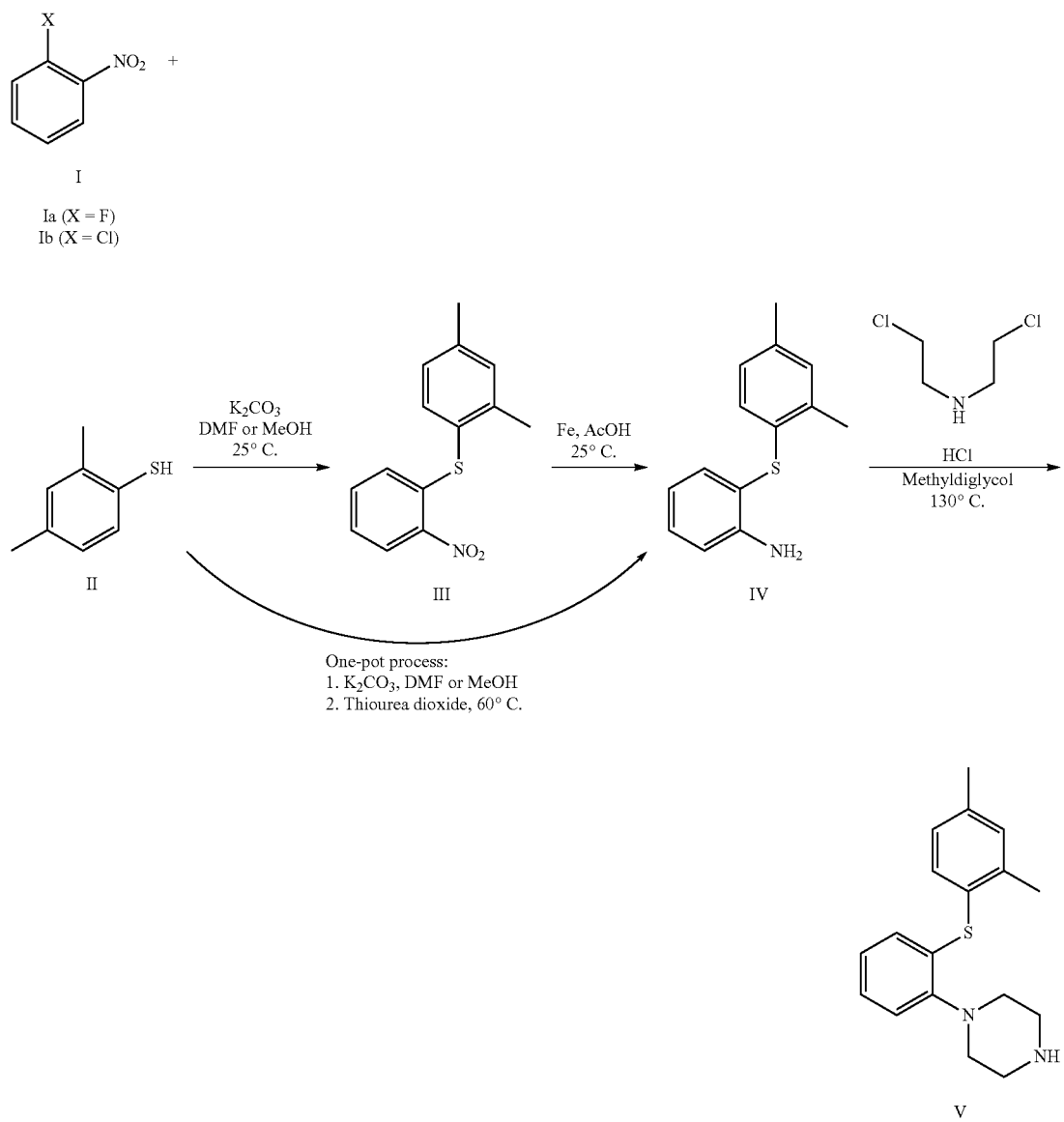

In the first reaction step, 1-fluoro-2-nitrobenzene (Ia) or 1-chloro-2-nitrobenzene (Ib) are used as starting material. Either Ia or Ib may be reacted with 2,4-dimethylthiophenol (II) in the presence of a base in any solvent to provide intermediate III. The base can be any organic or inorganic base, preferably $Na_2CO_3$ or $K_2CO_3$, and the solvent can be any protic or aprotic solvent. For the protic solvents preferably $C_1$-$C_6$ alcohols are used, most preferably methanol. For the aprotic solvents, preferably DMSO or DMF are used. The reaction can be performed at a temperature range of −30° C. to 100° C., more preferably at 0° C. to 50° C., more preferably still at 20° C. to 30° C., and most preferably at about 25° C.

In the second reaction step, the nitro group is reduced to the amino group to provide intermediate IV. The nitro reduction may be carried out using any of the known literature procedures, preferably Fe in AcOH, or Fe in mixtures of $C_1$-$C_6$ alcohols and AcOH, at 25° C.

The first two reaction steps can be comprised in a one-pot process. Intermediate IV can be prepared by the nucleophilic aromatic substitution of the halogen in I by starting material II, as described above, followed by the reduction of the nitro group using thiourea dioxide (also named formamidinesulfinic acid) or sodium dithionite at 25° C. to 150° C., preferably at 55° C. to 65° C., more preferably still at about 60° C. Compound IV can be isolated as a free amine or as a salt of the acid used, preferably HCl salt.

In the last reaction step vortioxetine (V) is made from intermediate IV. In this reaction step, the piperazine ring is formed using reagents such as bis(2-chloroethyl)amine free base or hydrochloride salt, diethanolamine or morpholine. Preferably, the reagent used in the final reaction step is bis(2-chloroethyl)amine hydrochloride salt in methyldiglycol at 25° C. to 200° C., preferably 100° C. to 150° C., more preferably at 120° C. to 140° C., most preferably at about 130° C.

The following Examples are non-limiting and serve to illustrate the invention.

Example 1

Preparation of (2,4-dimethylphenyl)(2-nitrophenyl)sulfane (III) from 1-fluoro-2-nitrobenzene (Ia)

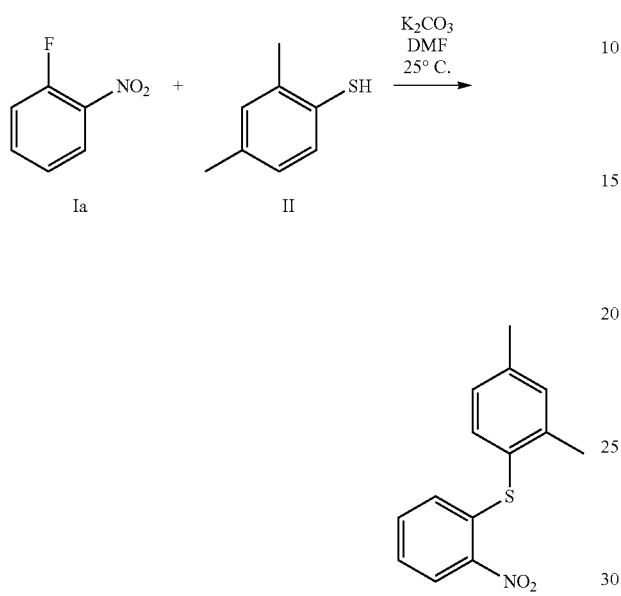

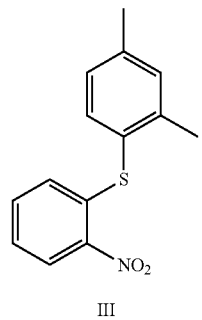

To a the mixture of K₂CO₃ (125 g, 0.90 mol) in dry DMF (0.5 L) while stirring at 25° C. was slowly added 2,4-dimethylbenzenethiol II (113 mL, 0.84 mol), then 1-fluoro-2-nitrobenzene Ia (116 g, 0.82 mol) was added in 2 h. After stirring the reaction mixture for 30 min 1 L water was added, and obtained mixture was stirred at 25° C. for 1 h. Yellow precipitate was then filtered off, washed with water (2×0.5 L) and dried in vacuum at 50° C. to afford title compound III as yellow crystals (m=209 g, 98% yield): DSC: Onset 93.34° C., Peak 97.39° C.; ¹H NMR (CDCl₃, 500 MHz) δ 2.30 (s, 3H), 2.40 (s, 3H), 6.71 (dd, J=1.2, 8.2 Hz, 1H), 7.11 (m, 1H), 7.18-7.22 (m, 2H), 7.32 (m, 1H), 7.46 (d, J=7.8 Hz, 1H), 8.25 (dd, J=1.4, 8.2 Hz, 1H); MS (ESI) m/z: 260 [MH]⁺.

Example 2

Preparation of (2,4-dimethylphenyl)(2-nitrophenyl)sulfane (III) from 1-chloro-2-nitrobenzene (Ib)

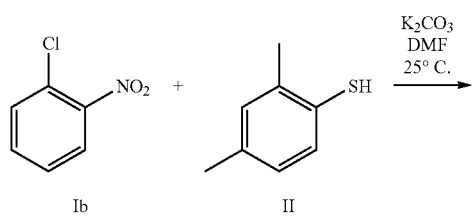

To a solution of 1-chloro-2-nitrobenzene Ib (5.00 g, 31.7 mmol) in dry DMF (30 mL) K₂CO₃ (5.26 g, 38 mmol) and 2,4-dimethylbenzenethiol II (4.50 mL, 33.3 mmol) were added, and resulting reaction mixture was stirred at 25° C. for 18 h. Water (60 mL) was added and obtained mixture was stirred at 25° C. for 30 min. Yellow precipitate was then filtered off, washed with water (2×50 mL) and dried to afford title compound III as yellow crystals (m=8.24 g, total yield): ¹H NMR (CDCl₃, 500 MHz) δ 2.30 (s, 3H), 2.40 (s, 3H), 6.71 (dd, J=1.2, 8.2 Hz, 1H), 7.11 (m, 1H), 7.18-7.22 (m, 2H), 7.32 (m, 1H), 7.46 (d, J=7.8 Hz, 1H), 8.25 (dd, J=1.4, 8.2 Hz, 1H); MS (ESI) m/z: 260 [MH]⁺.

Example 3

Preparation of 2-((2,4-dimethylphenyl)thio)aniline (IV)

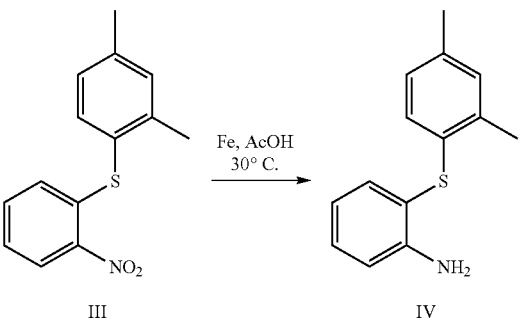

To a mixture of (2,4-dimethylphenyl)(2-nitrophenyl)sulfane III (10.0 g, 38.6 mmol) and AcOH (100 mL), Fe (8.61 g, 154 mmol) was added, and resulting reaction mixture was stirred at 30° C. for 16 h. Reaction mixture was then filtered through a bed of Celite, and filtrate was concentrated. To the residue 300 mL saturated NaHCO₃ and 100 mL EtOAc was added. Organic layer was separated, water layer was washed with EtOAc (100 mL), combined organic layers were dried over Na₂SO₄, and solvent was evaporated to afford title compound IV as orange oil (8.85 g, 99% yield): ¹H NMR (CDCl₃, 500 MHz) δ 2.28 (s, 3H), 2.40 (s, 3H), 4.24 (br s, 2H), 6.71 (d, J=8.1 Hz, 1H), 6.75-6.81 (m, 2H), 6.87 (m, 1H), 7.02 (m, 1H), 7.23 (m, 1H), 7.38 (dd, J=1.5, 7.7 Hz, 1H); MS (ESI) m/z: 230 [MH]⁺.

Example 4

Preparation of 2-((2,4-dimethylphenyl)thio)aniline hydrochloride (IVa)

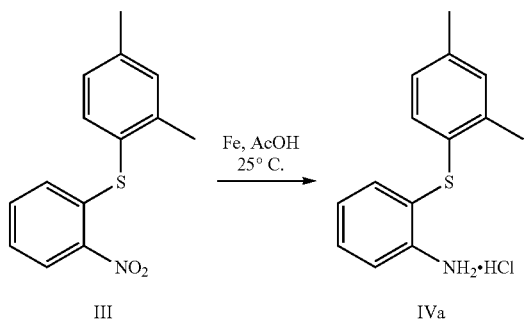

To a mixture of (2,4-dimethylphenyl)(2-nitrophenyl)sulfane III (1.00 g, 3.86 mmol) and AcOH (10 mL), Fe (0.86 g, 15.4 mmol) was added, and the resulting reaction mixture stirred at room temperature for 16 h. AcOH was then evaporated, 37% HCl (20 mL) was added, and the resulting reaction mixture stirred at room temperature for 15 min. Precipitate was then filtered off, washed with 1 M HCl (2×20 mL), and dried. Dry solid was then washed with EtOAc (2×20 mL) to afford title compound as white powder (m=0.68 g, 66% yield): $^1$H NMR (DMSO-d$_6$, 500 MHz) δ 2.24 (s, 3H), 2.28 (s, 3H), 6.97 (m, 2H), 7.00-7.07 (m, 2H), 7.12 (m, 1H), 7.27 (m, 1H), 7.37 (m, 1H), 8.79 (br s, 3H).

Example 5

Preparation of 1-(2-((2,4-dimethylphenyl)thio)phenyl)piperazine (vortioxetine, V)

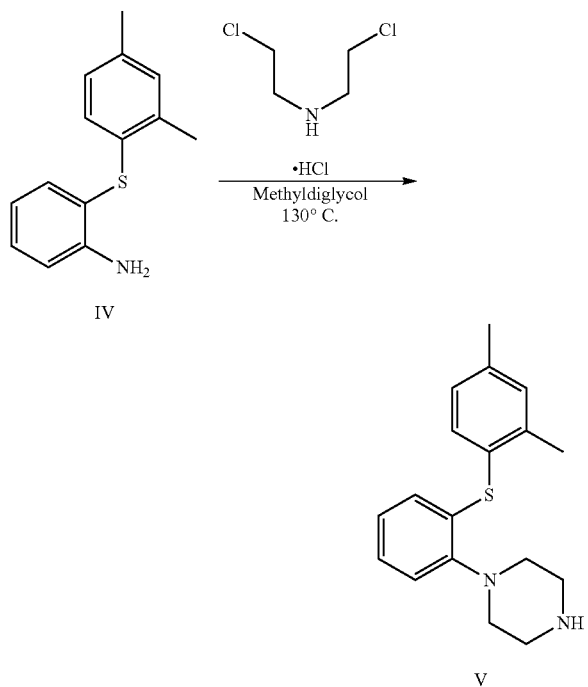

A mixture of 2-((2,4-dimethylphenyl)thio)aniline IV (5.0 g, 21.8 mmol), bis(2-chloroethyl)amine hydrochloride (3.89 g, 21.8 mmol) and diethylene glycol methyl ether (10 mL) was stirred at 130° C. for 3 days. Reaction mixture was then cooled to 25° C., water (20 mL) was added, and the mixture then further cooled to 10° C. while stirring. Precipitate was then filtered off, washed with water (10 mL), and dried. The solid was then washed with acetone (3×10 mL) and dried to afford vortioxetine hydrochloride as white powder (m=3.87 g, 53% yield).

A mixture of vortioxetine hydrochloride (3.5 g, 10.5 mmol), MeTHF (20 mL) and 1 M NaOH (20 mL) was stirred at room temperature for 1 h. Organic layer was then separated and water layer was extracted with MeTHF (2×20 mL). Combined organic layers were dried over Na$_2$SO$_4$, and solvent was evaporated to give brownish oil, which crystalized upon standing to give vortioxetine (V) as colorless crystals (m=2.84 g, 91% yield): DSC: Onset 115.69° C., Peak 116.71° C.; $^1$H NMR (CDCl$_3$, 500 MHz) δ 1.63 (br s, 1H), 2.33 (s, 3H), 2.37 (s, 3H), 3.02-3.09 (m, 8H), 6.52 (m, 1H), 6.87 (m, 1H), 7.04 (m, 1H), 7.06-7.10 (m, 2H), 7.16 (m, 1H), 7.39 (d, J=7.8 Hz, 1H); MS (ESI) m/z: 299 [MH]$^+$.

Example 6

Preparation of 1-(2-((2,4-dimethylphenyl)thio)phenyl)piperazine hydrobromide (vortioxetine HBr, VI)

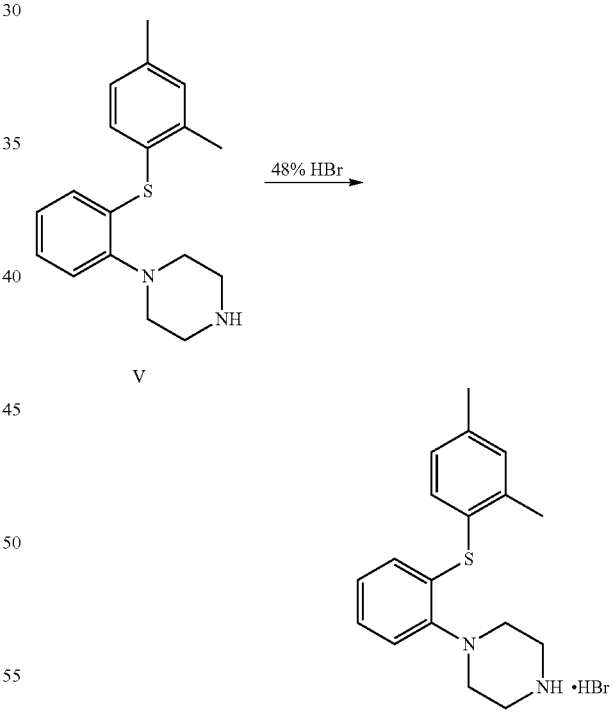

To a solution of vortioxetine V (1.80 g, 6.03 mmol) in iPrOAc (20 mL) at room temperature 48% HBr (0.68 mL, 6.03 mmol) was slowly added. Obtained mixture was stirred at room temperature for 1 h, white precipitate was then filtered off, washed with acetone (2×20 mL), and dried to afford title compound as white powder (m=2.15 g, 94% yield): DSC: Onset 221.74° C., Peak 223.86° C.; $^1$H NMR (DMSO-d$_6$, 500 MHz) δ 2.23 (s, 3H), 2.32 (s, 3H), 3.15-3.27

(m, 8H), 6.40 (m, 1H), 6.96 (m, 1H), 7.08-7.17 (m, 3H), 7.24 (m, 1H), 7.32 (d, J=7.8 Hz, 1H), 8.85 (br, 2H).

The invention claimed is:

1. A process for the manufacture of a compound of formula (IV), or salt thereof,

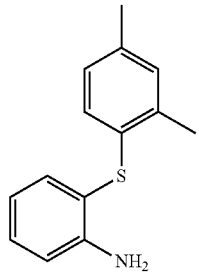

(IV)

which comprises the reduction of a compound of formula (III), or salt thereof,

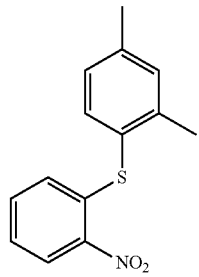

(III)

wherein the reducing agent is thiourea dioxide, sodium dithionite, iron or zinc.

2. A process according to claim 1 which comprises the additional step of reacting the compound of formula (IV) or salt thereof, with a piperazine ring forming agent, to provide a compound of formula (V), or salt thereof,

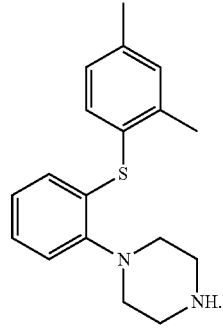

(V)

3. A process according to claim 2 wherein the piperazine ring forming agent is selected from bis(2-chloroethyl)amine or a salt thereof, diethanolamine and morpholine.

4. A process according to claim 2 which comprises the additional step of converting the compound of formula (V), or salt thereof, to its hydrobromide salt.

* * * * *